United States Patent [19]

Albert

[11] 4,032,787

[45] June 28, 1977

[54] METHOD AND APPARATUS PRODUCING PLURAL IMAGES OF DIFFERENT CONTRAST RANGE BY X-RAY SCANNING

[76] Inventor: Richard D. Albert, 317 Hartford Road, Danville, Calif. 94526

[22] Filed: Apr. 5, 1976

[21] Appl. No.: 673,908

Related U.S. Application Data

[63] Continuation-in-part of Ser. No. 481,954, June 24, 1974, Pat. No. 3,949,229.

[52] U.S. Cl. .......................... 250/402; 250/416 TV
[51] Int. Cl.² ........................................ G03B 41/16
[58] Field of Search .............. 250/401, 402, 416 R, 250/416 TV, 403, 404, 405; 178/DIG. 5

[56] References Cited

UNITED STATES PATENTS

| | | | |
|---|---|---|---|
| 3,342,933 | 9/1967 | Zieler | 250/416 TV |
| 3,582,651 | 6/1971 | Siedband | 250/416 TV |

*Primary Examiner*—Craig E. Church
*Attorney, Agent, or Firm*—Phillips, Moore, Weissenberger, Lempio & Majestic

[57] ABSTRACT

A plurality of radiographic images of a subject are obtained simultaneously by situating the subject between a scanning x-ray source and an x-ray detector. The source has an electron beam which is swept through a raster pattern on a broad target to produce a moving x-ray origin point while the detector has an effective radiation sensitive area which is very small in relation to the raster pattern. The X-axis and Y-axis beam deflection signals which control the x-ray source are also transmitted to each of a plurality of x-y display oscilloscopes causing each oscilloscope to exhibit a raster pattern similar to that of the x-ray source. The light intensity control of each oscilloscope receives processed x-ray count signals from the detector so that a radiographic image of the scanned region of the subject is generated at the screen of each oscilloscope. Separate signal processing circuits having different gain factors and establishing different base levels and peak levels for intensity signals are coupled between each oscilloscope and the x-ray detector enabling each radiograhic image to emphasize a different aspect of the scanned region of the subject as each image may have a different contrast range. The plural images taken in conjunction exhibit contrast ranges which may exceed the contrast limitations of a single oscilloscope or the similar limitations of photographic film which may be used to record the oscilloscope display.

10 Claims, 1 Drawing Figure

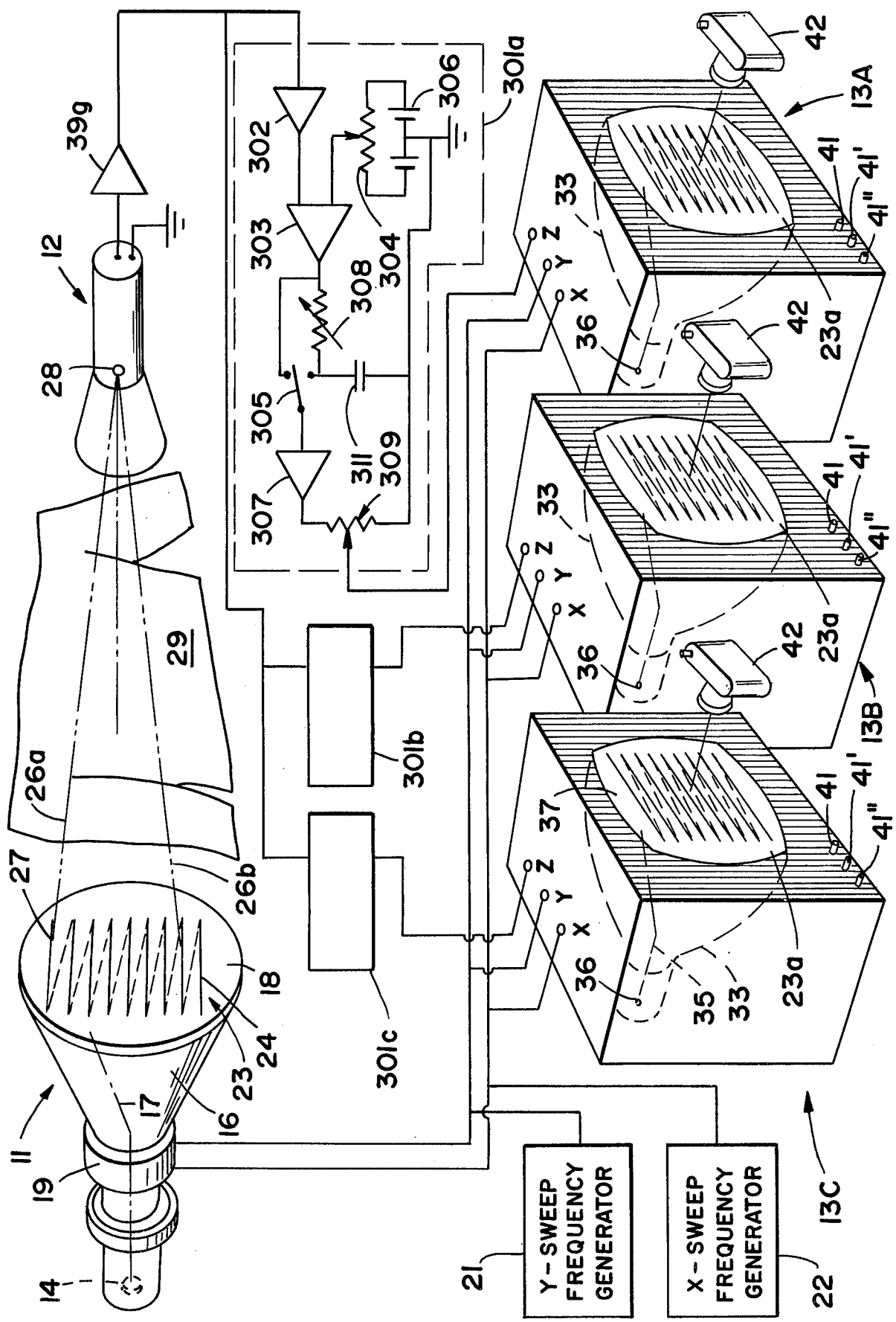

METHOD AND APPARATUS PRODUCING PLURAL IMAGES OF DIFFERENT CONTRAST RANGE BY X-RAY SCANNING

CROSS REFERENCE TO RELATED APPLICATION

This application is a continuation-in-part of my copending application Ser. No. 481,954, now U.S. Pat. No. 3,949,229 filed June 24, 1974, and entitled "X-ray Scanning Method and Apparatus".

BACKGROUND OF THE INVENTION

This invention relates to radiography and more particularly is to a scanning X-ray system and method for simultaneously producing a plurality of radiographic images from a single scanning X-ray exposure of the subject in which the several images exhibit widely varying contrast range characteristics to emphasize different aspects of the same region of the subject.

Conventional X-ray imaging systems in which the subject is situated between a fixed point X-ray source and a photographic film or fluorescent screen, are undersirably limited in the range of contrast obtainable in the image produced by a single exposure of the subject to X-rays. In the absence of the apparatus and techniques to be hereafter described, this is also true of a scanning X-ray system in which the subject is situated between a point source of X-rays which sweeps through a raster pattern while a relatively small area X-ray detector controls light intensity at the screen of an oscilloscope undergoing a similar raster pattern to generate a radiographic image at the screen of the oscilloscope. While oscilloscopes customarily have contrast and brightness controls, these must be set at some particular value during a single exposure of the subject. If these values are set to emphasize slight differences of X-ray absorbancies in the scanned area of the subject, such as differences between a tumor and healthy tissue in a medical patient, then other areas of widely differing X-ray absorbancy such as bony structures and adjacent soft tissue are obscured in the image. If controls are set to contrast areas of the subject of widely different X-ray absorbancy, then the areas of slight difference are obscured.

In general, most X-ray imaging systems are limited in their dynamic range of contrast to one or two orders of magnitude. Repeated exposures of the subject must be made to obtain desired information in many cases. In the case of the scanning system, as briefly described above, this does not result from any lack of information content in the signals produced by the X-ray detector in the course of a single scan of the subject, but instead derives from the limitations in the associated signal processing and display means, including the limited gray scale range of the oscilloscope screen and the limited contrast capabilities of photographic film which may be used to photograph the display on the oscilloscope screen.

SUMMARY OF THE PRESENT INVENTION

This invention alleviates the problem discussed above by providing for the simultaneous generation of a plurality of radiographic images of a given region of a subject, wherein each image may exhibit different contrast range characteristics. This is accomplished by employing a plurality of X-Y display devices, such as cathode-ray tube oscilloscopes or the like, each of which preferably has individual brightness and contrast controls and each of which receives the same X-axis and Y-axis deflection signals that control the scanning X-ray source. Thus, a moving point of light generation of the screen of each oscilloscope simultaneously sweeps through a raster pattern similar to that of the moving X-ray origin point at the X-ray source. The intensity of the point of light at each oscilloscope is controlled by the output of the X-ray detector, so that a radiographic image of the scanned region of the subject is produced at the screen of each oscilloscope.

To cause the image at each oscilloscope to exhibit a contrast range occupying a different portion of the full potential dynamic range of contrast contained in the X-ray detector output signals, an individual signal processing circuit is coupled between the detector and each oscilloscope intensity signal terminal. Each such circuit may have a different gain factor which is preferably adjustable and each such circuit may provide for different intensity signal base levels and peak levels. In a preferred form, means are provided for selectively connecting a pulse integrating circuit into the X-ray count signal path to the associated oscilloscope, so that the system may be operated either on an individual X-ray count basis or on a detected X-ray flux level basis.

Accordingly, it is an object of this invention to provide for greater utilization of the information content generated in a scanning X-ray system.

It is another object of this invention to provide for the simultaneous production of plural images by a scanning X-ray system, wherein each image may exhibit different contrast ranges.

The invention, together with further objects and advantages thereof, will best be understood by reference to the following description of a preferred embondiment taken in conjunction with the accompanying drawing.

BRIEF DESCRIPTION OF THE DRAWING

The accompanying drawing is a diagramatic view of a scanning X-ray system embodying the invention, wherein salient mechanical structures utilized in the system are shown in perspective form and electrical circuit elements are shown schematically.

DESCRIPTION OF A PREFERRED EMBODIMENT

My above identified copending application Ser. No. 481,954, filed June 24, 1974 and entitled "X-ray Scanning Method and Apparatus" is hereby incorporated by reference and made a part of the present application, said copending application will issue Apr. 6, 1976, as U.S. Pat. No. 3,949,229.

Referring now to the accompanying drawing, component elements of the plural image scanning X-ray system may include a scanning X-ray source 11, and X-ray detector assembly 12 and a plurality of electronic image producing means, which may be cathode-ray tube oscilloscopes 13A, 13B, and 13C or other equivalent x-y display devices.

The X-ray source 11 may be a part similar to a cathode-ray tube of the form having a cathode 14 at one end of an evacuated tube or envelope 16 from which electrons are accelerated in a beam 17 towards a broad anode or target plate 18 at the opposite larger end of the envelope. Beam deflection means such as a magnetic beam deflector coil assembly 19 is controlled by a Y-axis sweep frequency generator 21 and an X-axis sweep frequency generator 22 causing the electron beam 17 to scan the inner surface of target plate 18 in a raster pattern 23, in which the point of impact of the electron beam on the target plate is sequentially swept along a series of parallel spaced apart substantially linear scan lines 24. The scan lines 24 as depicted in the drawing, are fewer in number and more widely spaced apart than is generally the case in practice in order to more clearly illustrate the method of operation. Target plate 18 of the X-ray source, is formed at least in part of a material, such as copper, for example, which emits X-rays 26 upon being bombarded by high energy electrons. Thus, source 11, in effect, provides a moving point source of X-rays which may be systematically swept through the raster pattern 24.

The X-ray detector 12 may be of any of several known forms which produce output pulses indicative of individual X-ray counts or which produce an output signal indicative of the quantity of X-rays impinging on a radiation sensitive area 28, the detector being a scintillation detector in this particular example. The effective radiation sensitive area 28 of the detector should be substantially smaller than the area of the raster pattern 23 of the X-ray source 11. Preferably, the active sensitive area 28 of the detector should be as small as possible in relation to raster pattern 23, with due regard to obtaining an adequate response from the acceptable radiation flux level, as the difference in size of the sensitive area 28 and that of raster pattern 23, is a significant factor in determining definition in the radiographic images which are produced.

The X-ray detector 28 and the X-ray source 11 are spaced apart in order that a subject 29 to be examined may be situated between the source and detector in the path of X-ray radiation traveling from source target plate 18 towards the sensitive area 28 of the detector. In the present example, the subject 29 is the chest region of a medical patient, however, it should be understood that the invention is equally applicable to the production of radiographic images of other subjects, including inanimate objects, such as metallurgical castings, for example which are to be examined for internal flaws.

The system may operate on either a pluse basis or on a continuous signal basis depending on the general level of the radiation flux transmitted through the subject and received by the detector 12. If the radiation flux level produced by the source 11 is kept sufficiently low that simultaneous receipt of a number of X-rays at detector 12 is infrequent, then the detector may be of the form producing a discrete output pulse for each individual detected X-ray. If the X-ray flux output of the source 11 is higher, so that there are normally a sizable number of X-rays being received at the detector 12, the detector may be of the form which produces a more or less continuous output signal having a voltage or current proportional to the instantaneous magnitude of detected X-ray radiation.

Each of the image producing display means 13A, 13B and 13C may be an X-Y display oscilloscope of conventional construction and thus each such device may have a cathode-ray tube 33 with a large anode end defining a screen 37 which is formed in part of a phosphor material which emits visible light in response to bombardment by an electron beam 35 emitted from a cathode 36 in the opposite end of the tube. If the images which are produced at the screens 37 of the oscilloscopes are to be viewed directly, the oscilloscopes may be of the form having a selectable persistence control 41. A separate camera 42 may be disposed to view each screen 37 in order to photographically record the display on the screen in which case persistence controls may not be needed. Oscilloscopes 13 are preferably of the form having additional controls 41' for adjusting contrast and additional controls 41" for adjusting brightness.

The X-axis or horizontal sweep signal terminal X of each oscilloscope 13 is coupled to the previously described X sweep frequency generator 22 while the Y axis or vertical sweep signal terminal Y is coupled to the previously described Y sweep frequency generator 21. Accordingly, each oscilloscope 13 undergoes a raster pattern scanning action similar to that of the X-ray source 11 and concurrently with the scanning action of the source. Thus, at any given instant, the point of impact of the electron beam 35 of each display means on the associated phosphor screen 37 corresponds with the point of impact of the electron beam 17 of the X-ray source on target plate 18 of the source. By utilizing the output signals of the X-ray detector 12 to modulate the intensity of the electron beam 35 of each oscilloscope 13, a radiographic image of the scanned region of subject 29 is produced on the screens of the oscilloscopes.

For this purpose, the output signals of detector 12 are initially amplified in a preamplifier 39g. An individual one of three signal processing circuits 301A, 301B and 301C is connected between the output of preamplifier 39g and the electron beam intensity control signal terminal Z of an associated individual one of the oscilloscopes 13A, 13B and 13C respectively. Each signal processing circuit 301 may have a similar internal construction and accordingly only one such circuit, 301A is depicted in detail in the drawing.

Each such pulse processing circuit 301A may include an adjustable gain pulse shaping amplifier 302 which is connected between amplifier 39g and one input of a broad band differential D.C. coupled amplifier 303. To provide for selectively adjusting the base level of X-ray count signals, the reference input of amplifier 303 is coupled to the movable tap of a potentiometer 304 which has a resistive element connected across a bipolar D.C. power supply 306.

At one position of a mode selector switch 305, the output of amplifier 303 is connected directly to the input of a signal amplitude limiter amplifier 307. Amplifier 307 is operated near the saturation point to limit the maximum amplitude of the X-ray count signals to a predetermined level. The output of amplifier 307 is connected to circuit ground through the resistive element of a potentiometer 309 which has a movable tap connected to the intensity control signal terminal Z of the associated one of the oscilloscopes 13A.

Mode selector switch has an alternate position at which output pulses generated by the X-ray detector are integrated to apply a varying voltage to the oscilloscope intensity terminal Z which is indicative of detector output current rather than individual X-ray counts. At the alternate switch position, the direct connection between amplifiers 303 and 307 is opened and a similar connection is established through a variable resistor 308. To complete the integrating circuit, a capacitor 311 is connected between circuit ground and the circuit junction between resistor 308 and switch 305. By adjusting the resistor 308, the time constant of integration may be selected.

The alternate mode of operation is utilized when the X-ray count rate at detector 12 is sufficiently high that individual counts cannot be processed due to pulse pile-up.

Thus, the functions provided by each signal processing circuit 301 include establishing a predetermined selectable base level, by adjustment of potentiometer 304, for the signals applied to the intensity terminal Z of the associated one of the oscilloscopes 13. The maximum level of the signals applied to the associated oscilloscope intensity terminal Z is set by peak limiting amplifier 307 while adjustment of potentiometer 309 allows the gain factor of the signal processing circuit to be selectively varied including providing for negative gain factors.

Since the output signal characteristics of each of the three signal processing circuits 301A, 301B and 301C may be separately adjusted to provide different gains, different base levels and different peak levels for the intensity control signals applied to each of the three oscilloscopes 13, the radiographic images produced at the screens 37 of the three oscilloscopes may be caused to exhibit different contrast characteristics to thereby emphasize different aspects of the scanned region of the subject 29. The range of contrasts which may be produced at an individual one of the oscilloscopes 13 by adjustment of the contrast control 41' and brightness control 41" thereof is limited by the gray scale factor of the oscilloscope and, if a camera 42 is used to record the display, is additionally limited by the contrast capabilities of the photographic film. However, by providing differing adjustments of the three signal processing circuits 301 as described above, simultaneous displays of images having an aggregate contrast range exceeding the capabilities of any one oscilloscope and camera may be realized.

While the invention has been disclosed with respect to a single representative embodiment, it will be apparent that many variations are possible and it is not intended to limit the invention except as defined in the following claims.

What is claimed is:

1. Apparatus for simultaneously producing plural radiographic images of a subject comprising:
    a scanning X-ray source having a broad target plate and an electron gun for directing an electron beam towards said target plate and having electron beam deflection means for sweeping said electron beam along said target plate in a first direction in reponse to a first sweep signal and a means for sweeping said electron beam in a second orthogonal direction in response to a second sweep signal to establish a moving origin point of X-rays on said target plate which sweeps through a raster pattern thereon,
    an X-ray detector spaced apart from said source whereby said subject may be disposed therebetween, said detector having an active radiation sensitive area which is substantially smaller than said raster pattern and having means for producing X-ray count signals in response to X-rays which impinge on said radiation sensitive area,
    a plurality of X-Y display devices each having a screen and means for producing a point of light thereon and having means for sweeping said point of light in a first direction in response to a first sweep signal and means for sweeping said point of light in a second orthogonal direction in response to a second sweep signal and means for warying the intensity of said point of light in response to an intensity signal,
    a first sweep frequency generator coupled to said X-ray source and to each of said display devices to supply said first sweep signal to each thereof,
    a second sweep frequency generator coupled to said X-ray source and each of said display devices to supply said second sweep signal thereto, and
    a plurality of signal processing circuits, each being connected to said X-ray detector and to an associated separate one of said display devices to supply said intensity signal to said associated one of said display devices, said signal processing circuits having means for establishing a different predetermined intensity signal range for each said display devices in response to output signals from said detector.

2. The apparatus defined in claim 1 wherein each of said signal processing circuits further comprises means for selectively varying the base level of the intensity signal applied to the associated one of said display devices.

3. The apparatus defined in claim 1 wherein each of said signal processing circuits has means for establishing a predetermined maximum amplitude for the intensity signals applied to the associated one of said display devices.

4. The apparatus defined in claim 1 wherein each of said signal processing circuits has a different amplification gain factor.

5. The apparatus defined in claim 4 further comprising means for individually adjusting said gain factor of each of said signal processing circuits.

6. The apparatus defined in claim 1 wherein each of said signal processing circuits has pulse integrating means for converting a sequence of X-ray count pulses to a voltage having a magnitude indicative of the output of said detector, and switch means for selectively connecting said integrating means into the signal path between said detector and the associated one of said display devices.

7. The apparatus defined in claim 1 further comprising means for simultaneously photographing said screens of each of said display devices.

8. A method of simultaneously producing plural radiographic images of the subject wherein said images may exhibit different contrast range characteristics, comprising the steps of:
    disposing said subject between a moving X-ray origin point and an X-ray detector,
    generating a point of light on each of a plurality of screens,
    synchronously sweeping said X-ray origin point and said points of light in similar raster patterns,
    modulating the intensity of a first of said points of light in response to variations of the output of said X-ray detector with an intensity signal which varies within a first range of signal amplitudes, and,
    modulating the intensity of a second of said points of light in response to said variations of the output of said X-ray detector with a second intensity signal which varies within a second different range of signal amplitudes.

9. The method defined in claim 8 further comprising the steps of modulating the intensity signal for a first of said points of light in accordance with a first gain factor and modulating the intensity signal for the second of said points of light in accordance with a second different gain factor.

10. The method defined in claim 9 further comprising establishing different base levels and different peak levels for said first and second intensity signals.

UNITED STATES PATENT AND TRADEMARK OFFICE
CERTIFICATE OF CORRECTION

PATENT NO. : 4,032,787
DATED : June 28, 1977
INVENTOR(S) : Richard D. Albert

It is certified that error appears in the above-identified patent and that said Letters Patent are hereby corrected as shown below:

Column 1, line 37      - "absorbancies" should read --absorbencies--.

Column 1, line 40      - "absorbancy" should read --absorbency--.

Column 1, line 43      - "absorbancy" should read --absorbency--.

Column 2, lines 35-36 - "embondiment" should read --embodiment--.

Column 2, line 40      - "diagramatic" should read --diagrammatic--.

Column 3, lines 19-20 - "ascintillation" should read --a scintillation--.

Column 5, line 66
(line 27 of claim 1) - "warying" should read --varying--.

Column 6, line 35
(line 4 of claim 6) - after "output", --current-- should be inserted.

Signed and Sealed this

Fifteenth Day of November 1977

[SEAL]

Attest:

RUTH C. MASON
Attesting Officer

LUTRELLE F. PARKER
Acting Commissioner of Patents and Trademarks